United States Patent
Blass

(10) Patent No.: US 8,338,382 B2
(45) Date of Patent: *Dec. 25, 2012

(54) METHOD OF TREATING IMPAIRED MITOCHONDRIAL FUNCTION

(75) Inventor: John P. Blass, New York, NY (US)

(73) Assignee: John Blass, New York, NY (US)

( * ) Notice: Subject to any disclaimer, the term of this patent is extended or adjusted under 35 U.S.C. 154(b) by 953 days.

This patent is subject to a terminal disclaimer.

(21) Appl. No.: 11/478,195

(22) Filed: Jun. 29, 2006

(65) Prior Publication Data

US 2006/0246155 A1   Nov. 2, 2006
US 2011/0300236 A9   Dec. 8, 2011

Related U.S. Application Data

(60) Division of application No. 10/838,128, filed on May 3, 2004, now abandoned, and a continuation-in-part of application No. 10/379,816, filed on Mar. 4, 2003, now abandoned, which is a continuation of application No. 09/529,091, filed as application No. PCT/US98/18120 on Sep. 1, 1998, now Pat. No. 6,537,969.

(60) Provisional application No. 60/063,165, filed on Oct. 24, 1997.

(51) Int. Cl.
*A61K 31/194* (2006.01)
*A61K 31/01* (2006.01)

(52) U.S. Cl. ............................ 514/23; 514/574; 514/733

(58) Field of Classification Search .................... 514/23, 514/574, 733
See application file for complete search history.

(56) References Cited

U.S. PATENT DOCUMENTS

| 5,455,276 A | 10/1995 | Sabelli |
| 5,739,117 A | 4/1998 | Yokoyama et al. |
| 5,948,443 A | 9/1999 | Riley et al. |
| 6,509,381 B2 | 1/2003 | Empie et al. |
| 6,537,969 B1 * | 3/2003 | Blass .............................. 514/23 |

FOREIGN PATENT DOCUMENTS

| CA | 2 306 875 | 5/1999 |
| CA | 2 395 695 | 7/2001 |
| CA | 2 401 383 | 8/2002 |
| CA | 2 510 788 | 7/2003 |
| EP | 0 059 057 | 9/1982 |
| JP | 57 110148 | 7/1982 |
| KR | 2004/0007174 | 1/2004 |
| WO | WO 99/59561 | 11/1999 |
| WO | WO 03/013566 | 2/2003 |
| WO | WO 03/079818 A1 | 10/2003 |

OTHER PUBLICATIONS

Canadian Office Action for Canadian Application No. 2,569,216 dated Sep. 5, 2008.
Office Action for U.S. Appl. No. 10/838,128 mailed Jul. 9, 2008.
Supplementary European Search Report for European Application No. EP 04 75 5210 dated May 4, 2009.
European Office Action for European Application No. 04755210.4, dated Aug. 20, 2010.

* cited by examiner

*Primary Examiner* — Zohreh Fay
(74) *Attorney, Agent, or Firm* — Pearl Cohen Zedek Latzer, LLP

(57) ABSTRACT

Disclosed in certain embodiments is a pharmaceutical composition comprising a sugar; a Krebs cycle intermediate, precursor of a Krebs cycle intermediate, salt thereof, or combination thereof; and a component selected from the group consisting of an unsaturated lipid, phenylethylamine, a soluble calcium compound, or a combination thereof.

24 Claims, 1 Drawing Sheet

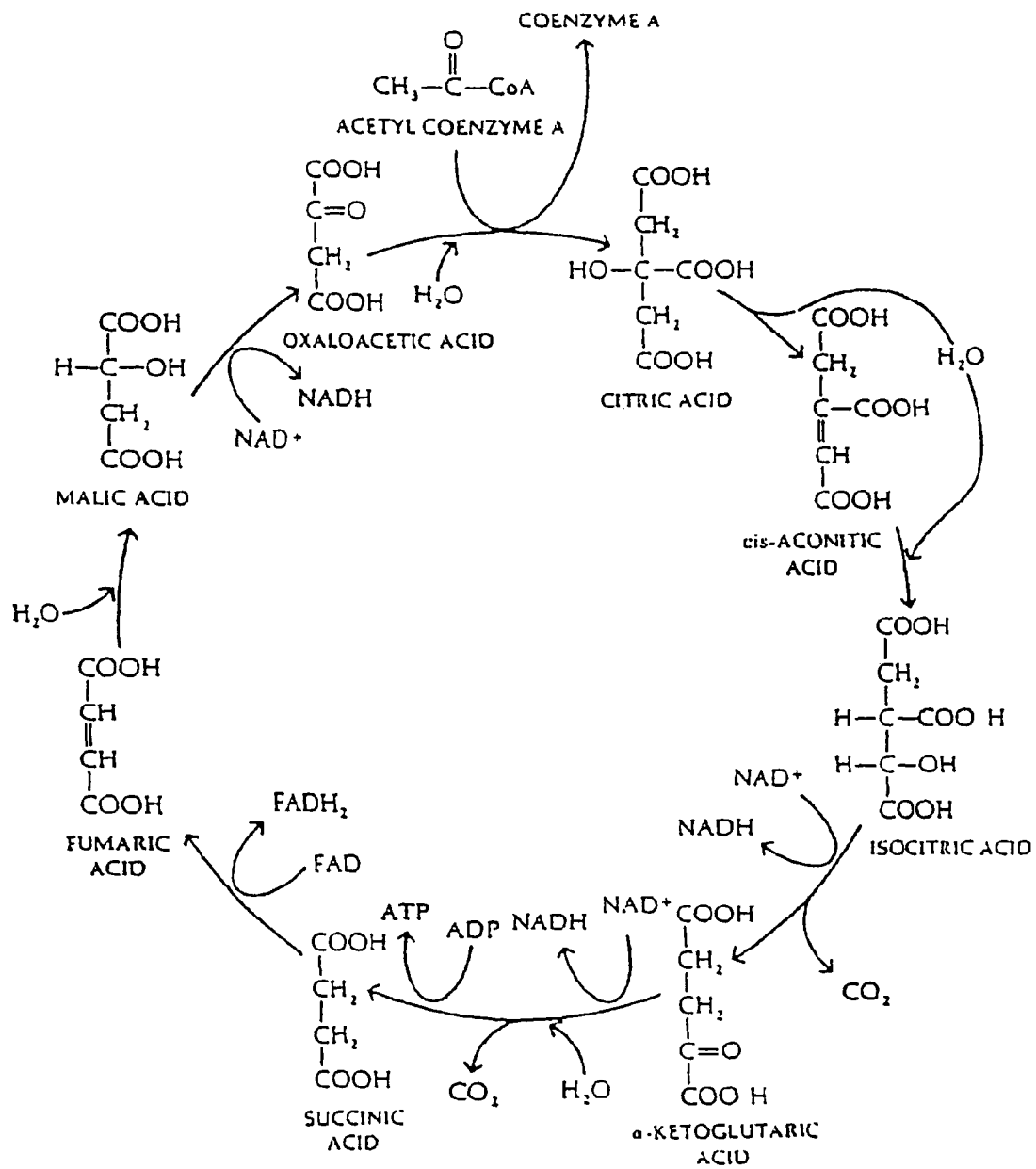

METHOD OF TREATING IMPAIRED MITOCHONDRIAL FUNCTION

CROSS REFERENCE TO RELATED APPLICATION

This application is a divisional of U.S. patent application Ser. No. 10/838,128, filed May 3, 2004 now abandoned, and is a continuation-in-part of U.S. patent application Ser. No. 10/379,816 filed on Mar. 4, 2003 now abandoned, which is a continuation of U.S. patent application Ser. No. 09/529,091, filed Oct. 20, 2000, now U.S. Pat. No. 6,537,969, which is a U.S. national phase application of International Patent Application No. PCT/US98/18120, filed Sep. 1, 1998, which claimed the benefit of U.S. Provisional Patent Application No. 60/063,165, filed Oct. 24, 1997.

FIELD OF THE INVENTION

The present invention relates to pharmaceutical compositions for individuals suffering from metabolic insufficiencies, e.g., cerebral and cardiac insufficiencies, and methods of treatment thereof.

BACKGROUND OF THE INVENTION

During normal operation of the catabolic process, energy is harvested and subsequently stored in a readily available form, namely, the phosphate bonds of adenosine triphosphate ("ATP"). When energy is required for anabolic processes, a phosphate bond of ATP is broken to yield energy for driving anabolic reactions and adenosine diphosphate ("ADP") is regenerated. The process of catabolism involves the breakdown of proteins, polysaccharides, and lipids. Proteins are broken into smaller peptides and constituent amino acids, polysaccharides and disaccharides are broken down into their monosaccharide constituents, and lipids are broken down into glycerol and the fatty acid constituents. These compounds are further broken down into even smaller compounds, principally, two-carbon acetyl groups.

The two-carbon acetyl group, an essential component in the catabolic process, is introduced into the Krebs tricarboxylic acid cycle ("Krebs cycle") via acetyl coenzyme A. The acetyl group serves as a carbon source for the final stages of catabolism. The Krebs cycle and an accompanying electron transport system involve a series of enzymatically controlled reactions that enable complete oxidation of the two-carbon acetyl group to form carbon dioxide and water. As shown in FIG. 1, acetyl groups are introduced into the Krebs cycle by bonding to oxaloacetic acid to form citric acid. During subsequent steps of the Krebs cycle, citric acid is converted into aconitic acid and then into isocitric acid. As isocitric acid is converted into ketoglutaric acid, one carbon atom is completely oxidized to carbon dioxide. As ketoglutaric acid is converted into succinic acid, a second carbon atom is completely oxidized to carbon dioxide. During the remaining steps, succinic acid is converted into flimaric acid, fumaric acid is converted into malic acid, and malic acid is converted into oxaloacetic acid. Each complete turn of the Krebs cycle harvests the energy of the acetyl group to yield one molecule of ATP, three molecules of nicotinamide adenine dinucleotide ("NADH"), and one molecule of flavin adenine dinucleotide $FADH_2$. The NADH and $FADH_2$ are subsequently used as electron donors in the electron transport system to yield additional molecules of ATP.

The Krebs cycle and the accompanying electron transport system occur in the mitochondria, which are present in different types of cells in varying numbers depending upon the cellular energy requirements. For example, neuronal and cardiac muscle cells have high numbers of mitochondria because they have extremely high energy requirements. Because of their high energy requirements, these types of cells are particularly vulnerable to disorders or conditions associated with a breakdown of the catabolic pathways or otherwise defective intracellular energy metabolism. Exemplary disorders or conditions include Alzheimer's Disease, Parkinson's Disease, Huntington's Disease and other neurodegenerative disorders (Beal et al., "Do Defects in Mitochondrial Energy Metabolism Underlie the Pathology of Neurodegenerative Diseases?," Trends Neurosci. 16(4):125-131 (1993); Jenkins et al., "Evidence for Impairment of Energy Metabolism in vivo in Huntington's Disease Using Localized $^1H$ NMR Spectroscopy," Neurol. 43:2689-2695 (1993)).

Alzheimer's Disease is one of the most common causes of disabling dementia in humans. Because Alzheimer's Disease is a progressive, degenerative illness, it affects not only the patients, but also their families and caregivers. In early stages of Alzheimer's Disease, activities of daily living are only minimally affected by cognitive or functional impairment, which may often be a first clinical sign of the disease (Small et al., "Diagnosis and Treatment of Alzheimer Disease and Related Disorders," Consensus Statement of the American Association for Geriatric Psychiatry, the Alzheimer's Association, and the American Geriatrics Society, JAMA 278: 1363-1371 (1997)). As Alzheimer's Disease progresses, the patients' ability to perform activities of daily living diminishes and the patients become increasingly more dependent upon caregivers and other family members (see Galasko et al., "An Inventory to Assess Activities of Daily Living for Clinical Trials in Alzheimer's Disease," Alzheimer Dis. Assoc. Disord. 11 (Suppl. 2):S33-S39 (1997)).

Parkinson's Disease is widely considered to be the result of degradation of the pre-synaptic dopaminergic neurons in the brain, with a subsequent decrease in the amount of the neurotransmitter dopamine that is being released. Inadequate dopamine release, therefore, leads to the onset of voluntary muscle control disturbances symptomatic of Parkinson's Disease. The motor dysfunction symptoms of Parkinson's Disease have been treated in the past using dopamine receptor agonists (including L-Dopa), monoamine oxidase binding inhibitors, tricyclic antidepressants, anticholinergics, and histamine H1-antagonists. Some investigators state that MAO inhibitors treat the primary disease process. The disease continues to progress and, frequently after a certain length of time, dopamine replacement treatment will lose its effectiveness. In addition to motor dysfunction, however, Parkinson's Disease is also characterized by neuropsychiatric disorders or symptoms. These include apathy-amotivation, depression, and dementia. Parkinson's Disease patients with dementia have been reported to respond less well to standard L-dopa therapy. Moreover, these treatments have little or no benefit with respect to the neuropsychiatric symptoms.

Huntington's Disease is a familial neurodegenerative disorder that afflicts about 1 in 10,000 individuals (Martin et al., "Huntington's Disease: Pathogenesis and Management," N. Engl. J. Med. 315:1267-1276 (1986); Gusella, "Huntington's Disease," Adv. Hum. Genet. 20:125-151 (1991)). Huntington's Disease is inherited in an autosomal dominant manner and is characterized by choreiform movements, dementia, and cognitive decline. The disorder usually has a mid-life onset, between the ages of 30 to 50 years, but may in some cases begin very early or much later in life. The symptoms are progressive and death typically ensues 10 to 20 years after onset, most often as the result of secondary complications of the movement disorder. The major site of pathology in Huntington's Disease is the striatum, where up to 90% of the neurons may be depleted. The impaired cognitive functions and eventual dementia may be due either to the loss of cortical neurons or to the disruption of normal activity in the cognitive portions of the basal ganglia. The characteristic chorea is believed to be caused by the neuronal loss in the striatum, although a reduction in subthalamic nucleus activity may also contribute.

Glutamate-induced neuronal cell death is believed to contribute to Huntington's Disease. Glutamate is the principal excitatory transmitter in the brain. It excites virtually all central neurons and is present in the nerve terminals in extremely high concentrations (over $10^{-3}$ M). Glutamate receptors are divided into four types (named after their model agonists): kainate receptors, N-methyl-D-aspartate ("NMDA") receptors, α-amino-3-hydroxy-5-methyl-4-isoxazolepropionate ("AMPA") receptors, and metabolotrophic receptors. Many normal synaptic transmission events involve glutamate release. However, glutamate can also induce neurotoxicity and neuronal death at high levels (Choi, "Glutamate Neurotoxicity and Diseases of the Nervous System," Neuron, 1:623-634 (1988)). The mechanism of cell death occurs primarily by the persistent action of glutamate on the NMDA receptors. These toxic changes produced by glutamate, called glutamate excitotoxicity, are believed to be a major cause of cell damage and death after acute brain injury such as stroke or excessive convulsions. It has been suggested that excitotoxicity may be involved in brain ischemia, Alzheimer's Disease and Huntington's Disease (Greenamyre et al., "Alterations in L-glutamate Binding in Alzheimer's and Huntington's Diseases," Science, 227:1496-1499 (1985); Choi, "Glutamate Neurotoxicity and Diseases of the Nervous System," Neuron, 1:623-634 (1988)).

The administration of agents that improve energy metabolism, and possibly prevent cell death, has been suggested for the treatment of disorders characterized by energy-deficient cells (Beal et al., "Do Defects in Mitochondrial Energy Metabolism Underlie the Pathology of Neurodegenerative Diseases?," Trends Neurosci. 16(4):125-131 (1993)). One approach to augmenting the energy level of energy-deficient cells (i.e., as a result of hypoxia or hypoglycemia) involves the administration of pyruvate, which is later converted to acetate during normal metabolism. According to U.S. Pat. No. 5,395,822 to Izumi et al. ("Izumi"), the administration of pyruvate to a patient before or after an ischemic event (i.e., which produces a state of hypoxia or hypoglycemia) is sufficient to prevent neuronal degradation that normally is associated with the ischemic event. Izumi also identified the administration of glucose prior to an ischemic event as undesirable, because its administration resulted in lactic acid accumulation, which is a factor contributing to brain damage.

An approach for the treatment of Alzheimer's Disease includes the administration of NADH or nicotinamide adenine dinucleotide phosphate ("NADPH"), or the salts thereof. The administration of NADH or NADPH is described in U.S. Pat. No. 5,444,053 to Birkmayer, which discloses the use of salts formed with various acids including, among others, malic acid, succinic acid, and acetic acid. Similar approaches to treating Parkinson's Disease using NADH and NADPH are described in U.S. Pat. Nos. 5,019,561 and 4,970,200, both to Birkmayer.

U.S. Pat. No. 6,537,969 by the present inventor is directed toward overcoming these above-noted deficiencies in treating conditions associated with a breakdown of the catabolic pathways or otherwise defective intracellular energy metabolism.

Another metabolic problem is obesity. Obesity has reached epidemic proportions in the United States (Hill J O, Wyatt Hr, Reed G W, Peters J C, Obesity and the environment: where do we go from here? *Science* 2003; 301:598; Bray G A, Evaluation of obesity: Who are the obese?. Postgrad Med 2003; 114:19-27; Wyatt H R, The prevalence of obesity, Prim Care 2003; 30: 267-279) and in the rest of the world (Zimmerman-Belsing T, Feldt-Rasmussen U, Obesity: the new worldwide epidemic threat to general health and our complete lack of effective treatment, Endocrinology 2004; 145:1501-1502). The best available data indicate that, in 2004, over 60% of the total U.S. population is overweight or obese. The epidemic of obesity involves children and adolescents as well as adults and the elderly. All indications are that obesity is becoming more severe, not less. Obesity is recognized to be the major nutritional problem in the U.S. today and may be, or is fast becoming, the most important current public health problem in this country.

Studies of the causes of obesity and specifically of feeding behavior, including hunger and satiety, are extensive. The mechanisms involved are complex at the levels of brain anatomy, physiology, pharmacology, endocrinology, biochemistry and molecular biology. Certain relatively simple generalizations can, however, be validly made. Obesity is the result of ingesting more energy in the form of calories in food than is expended in the normal activities of the body, including exercise. (In other words, the first law of Thermodynamics holds.) If the amount of food is not limited, people eat until they are satisfied. The relationship among amount and type of food ingested, nutritional needs defined in terms of physiology, and satisfaction with eating (satiation) is very complex. It involves emotional as well as "rational" factors. For instance, change in the amount of food ingested can be a sign of depression or mania or other disorders affecting mood/affect. At a milder level, "binge eating" is a well-known response to emotional, professional and other stresses.

Amphetamine is a "weight loss" medication that has been useful in controlling excessive appetite and the resulting obesity, but that is not now used for this purpose because of its side effects (Makris A P, Rush C R, Frederich R C, Kelly T H, Wake-promoting agents with different mechanisms of action: comparison of effects of madafinil and amphetamine on food intake and cardiovascular activity, Appetite 2004; 42: 185-195; Kuo D Y, Further evidence for the mediation of both subtypes of dopamine D1/D2 receptors and cerebral neuropeptide Y (NPY) in amphetamine-induced appetite suppression, Behav Brain Res 2003; 147: 149-155). It can cause dangerous changes in the heart including cardiac death, and it can easily over-stimulate the brain. Chronic amphetamine use can cause a syndrome that resembles schizophrenia. Therefore, there is a need for an alternative approach that utilizes the effects of amphetamine in combating overweight/obesity without incurring the unacceptable side effects of amphetamine itself.

2-Phenylethylamine (β-phenylethylamine) is a normal constituent of the diet that has "amphetamine-like" affects, but is much less potent than amphetamine itself and is not dangerous (Kato M, Ishida K, Chuma T, Abe K, Shigenaga T, Taguchi K, Miyatake T, β-Phenylethylamine modulates acetylcholine release in the rat striatum: involvement of a dopamine D(2) receptor mechanism, Eur J Pharmacol 2001; 418: 65-71; Gianutsos G, Chute S, Pharmacological changes induced by repeated exposure to phenylethylamine, Pharmacol Biochem Behav 1986; 25: 129-134; Kuroki T, Tsutsumi T, Hirano M, Matsumoto T, Tatebayashi Y, Nishiyama K, Uchimura H, Shiraishi A, Nakahara T, Nakamura K, Behavioral sensitization to β-phenylethylamine (PEA): enduring modifications of specific dopaminergic neuron systems in the rat, Psychopharmacology 1990; 102: 5-10; Barroso N, Rodriguez M, Action of β-phenylethylamine and related amines on nigrostriatal dopamine neurotransmission, Eur J Pharmacol 1996; 297: 195-203). 2-Phenylethylamine ("2PE") is a normal constituent of chocolate and of many cheeses, among other foodstuffs. 2PE is present in chocolate itself at about 60 μg/gm chocolate or more, and significantly higher in unprocessed cocoa and a number of cheeses (Baker G B, Wong J T, Coutts R T, Pasutto F. Simultaneous extraction and quantitation of several bioactive amines in cheese and chocolate, J Chromatogr 1987; 392: 317-31). A "chocolate binge" could lead to the ingestion of about 3 mg of 2PE. Experimental animals have ingested amounts of 2PE over 10,000 times higher than this for months (Kuroki T, Tsutsumi T, Hirano M, Matsumoto T, Tatebayashi Y, Nishiyama K, Uchimura H, Shiraishi A, Nakahara T, Nakamura K, Behavioral sensitization to β-phenylethylamine (PEA): enduring modifications of specific dopaminergic neuron systems in the rat, Psychopharmacology 1990; 102: 5-10). 2PE stimulates, albeit more weakly, the same dopamine (D1 and D2) receptors that amphetamine stimulates. Some of the medicinal effects of chocolate and other preparations of the cocoa bean have been attributed to 2PE, notably the satisfying and calming aspects. 2PE appears to have a mild anti-depressant affect (Paetsch P R, Greenshaw A J, 2-Phenylethylamine-induced changes in catecholamine receptor density: implications for antidepressant drug action, Neurochem Res 1993; 18: 1015-1022). 2PE levels are not consistently altered in patients with psychosis (Szymanski H V, Naylor E W, Karoum F, Plasma phenylethylamine and phenylalanine in chronic schizophrenic patients, Biol Pyschiat 1987; 22: 194-198).

One of the major problems in treating obesity is the tendency for people to regain the weight they have lost. Animal studies indicate that this effect is due at least in part to inadequate stimulation of dopamine receptors in the brain after weight loss. Pothos et al. concluded that "Low extracellular DA [dopamine] may also underlie the increase in food and drug intake typically observed in underweight animals and humans when they attempt to restore extracellular DA levels by natural or artificial means." (Pothos E N, Creese I, Hoebel B G, Restricted eating with weight loss selectively decreases extracellular dopamine in the nucleus accumbens and alters dopamine response to amphetamine, morphine, and food intake, J Neurosci 1995; 15: 5540-6650.) These observations are in accord with extensive data on humans who regain weight after weight loss, even though available techniques do not allow direct measurement of these parameters in the brains of living humans. The drive to eat too much reflects the chemistry of the brain, not the nutritional needs of the whole body. The alteration in brain chemistry drives the harmful excess intake of calories. The obvious treatment is to feed a material that restores the physiological action in the brain that was diminished by weight loss, and does so without inducing unacceptable side effects. The action of the low extracellular DA can presumably be restored by feeding either precursors of dopamine (notably L-DOPA) or mimics of dopamine actions such as amphetamine. Though L-DOPA has been used (usually with carbidopa) to treat Parkinson's Disease, it has well known and severe side effects that limit its use even for that disease. The unacceptable side effects of amphetamine as a weight loss medication have been discussed above. Ingestion of 2PE in low mg amounts allows the mimicking of the action of extracellular DA without significant side effects.

Chocolate is now accepted to have additional beneficial health effects due to its contents of antioxidants. (The sweet science: dark chocolate may be good for you, Harv Health Lett. 2004; 29:7; Lee K W, Kim Y J, Lee H J, Lee C Y, Cocoa has more phenolic phytochemicals and a higher antioxidant capacity than teas and red wine, J Agric Food Chem. 2003; 51: 7292-5.) These health effects are apart from its effects on mood and satiety, which are more reasonably attributed to its content of 2PE. Polyphenols are antioxidants that are found in both chocolate and red wine and have beneficial effects (Lee K W, Kim Y J, Lee H J, Lee C Y, Cocoa has more phenolic phytochemicals and a higher antioxidant capacity than teas and red wine, J Agric Food Chem. 2003; 51: 7292-5; Constant J, Alcohol, ischemic heart disease, and the French paradox, Clin Cardiol. 1997; 20: 420-4).

The addition of a Krebs tricarboxylic acid cycle substrate (such as malate) and of a source of substrate (pyruvate derived from glucose) can be expected to enhance the antioxidant activity of the antioxidant compounds found in chocolate, since the combination of glucose and a Krebs cycle substrate can be expected to enhance the ability of the brain cells to generate the reducing equivalents needed to carry out antioxidant activities. Calculations of free radical production in normal humans indicate that it is impossible to ingest enough "antioxidant" to significantly reduce the burden of free radicals produced during normal human metabolism. The "priming" of the parts of the cells that produce the reducing equivalents necessary to regenerate antioxidants is therefore critical. Glucose and malate are particularly appropriate for producing the desired effect, since both cross easily into the brain across the "blood-brain barrier." Use of glucose rather than another sugar has the advantage that it promptly elevates blood glucose and thereby brain glucose, increasing satisfaction and satiation and providing an "energy boost."

In preparing a form of chocolate that contains added 2PE, as well as glucose, calcium malate, and added antioxidant as disclosed herein, it is advisable to use a vegetable oil to allow the mixing together of the ingredients. A particularly healthy form of vegetable oil is that from flax seed, due to its contents of ω-3 fatty acids (Bloedon L T, Szapary P O, Flaxseed and cardiovascular risk, Nutr Rev 2004; 62: 18-27; Prasad K, Dietary flax seed in prevention of hypercholesterolemic atherosclerosis, Atherosclerosis 1997; 132: 69-76).

Phenylethylamine (PEA), is also found in some red wines, promotes energy and elevates mood. A deficiency in PEA renders the person weak, tired, sluggish and depressed. Taking PEA rapidly restores well-being. PEA is a natural, physiological treatment of depression. Approximately 60% of depressed patients have a reduction in PEA metabolism, and PEA is effective in 60% of depressed patients. PEA relieves depression rapidly, in a matter of hours or days, and produces no toxic effects, tolerance or abuse. PEA controls depression in 60% of depressed persons—the same percentage as major antidepressants such as Prozac—but is less toxic. See Sabelli, H. (2002). Phenylethylamine deficit and replacement in depressive Illness. In D. Mishooulon and J. F. Rosenbaum. (Eds.), Natural medications for psychiatric disorders. (pp 83-110), Baltimore: Lippencott Williams and Wilkins; also see Sabelli, H. (2000). Aminoacid precursors for depression. Psychiatric Times, 17. 42-49.

Lipids are concentrated sources of energy as well as structural components of cell membranes. Everybody needs a certain amount of dietary fat for normal body functions. When fats are digested, emulsified and absorbed, they facilitate the intestinal absorption and transport of fat soluble vitamins A, D, E and K. They are also used to cushion and protect the heart, kidneys and liver. In certain climates, subcutaneous body fat helps to insulate the body from the cold and prevent heat loss through the skin. These functions can be met by a daily intake of 15 to 25 grams of fat. Lipids provide the body with maximum energy (9 kcal per gram), approximately twice that for an equal amount of protein or carbohydrates.

Lipids enter the body through the mouth and pass to the stomach, but are little affected by its acidic environment. They are absorbed primarily in the small intestines, where they are emulsified by salts of the bile acids and are hydrolyzed to fatty acids and glycerol by various water-soluble enzymes (lipases). From the intestines, the hydrolyzed lipids enter the bloodstream and are transported to other organs, mainly the liver, for further metabolism. Ultimately the fatty acids may be degraded to carbon dioxide and water to furnish energy.

There are many types of fatty acids, but they can be divided into three groups—saturated fats, monounsaturated fats and polyunsaturated fats. Polyunsaturated fats include ω-3 and ω-6 fatty acids, among others. Intake of ω-3 and ω-6 fatty acids is known to protect against atherosclerosis, which contributes to metabolic insufficiency in the brain, heart and other tissue by impairing their blood supply. A major polyunsaturated fatty acid is arachidonic acid, which is neither ω-3 nor ω-6.

There exists a need in the art for pharmaceutical compositions that provide the combined benefits of the pharmaceutical formulations of U.S. Pat. No. 6,537,969 with the benefits of phenylethylamine, antioxidants and/or unsaturated lipids (e.g., ω-3 and ω-6 fatty acids). There exists a further need in the art to improve palatability of the pharmaceutical formulations of U.S. Pat. No. 6,537,969.

All documents referred to herein are incorporated by reference in their entireties for all purposes.

SUMMARY OF THE INVENTION

The present invention in certain embodiments is directed to a pharmaceutical composition which includes a sugar, a Krebs cycle intermediate or salt thereof, or a precursor of a Krebs cycle intermediate; and a component selected from the group consisting of an unsaturated lipid, phenylethylamine, a soluble calcium compound, or a combination thereof. The present invention in certain embodiments is directed to chocolate products (e.g., a chocolate bar or a chocolate drink) fortified with added 2-phenylethylamine in order to make a small amount of the satisfying product at the cost of little intake of calories amounts. In certain embodiments, the ratio of the amount of 2-phenylethylamine present in the fortified product as compared to the amount in a comparable non-fortified product can be at least 2:1; at least 10:1; at least 50:1; at least 100:1; at least 500:1; or at least 1000:1.

The present invention in certain embodiments is also directed to a method of treating impaired mitochondrial function while simultaneously providing the additional benefits (e.g., improvement in cerebral and/or cardiac function) of unsaturated lipids and phenylethylamine as discussed herein. The method includes administering certain pharmaceutical compositions of the present invention to a subject in need thereof.

The present invention in certain embodiments is also directed to a method of treating impaired mitochondrial, cerebral and/or cardiac function with a pharmaceutical formulation which is palatable to a patient in need thereof.

The present invention further relates to a method of improving cerebral function in an individual having impaired cerebral metabolism. This method includes administering a pharmaceutical composition of the present invention to a subject in need thereof.

The pharmaceutical compositions of the present invention are particularly desirable for the prophylaxis or treatment of disorders associated with impaired mitochondrial function while simultaneously providing weight loss, increased energy and mood, and/or a desirable lipid profile. Disorders that can be treated include conditions or diseases characterized by a decreased level of oxidative metabolism, such as conditions or diseases of the nervous system, conditions or diseases of other parts of the body (e.g., cardiovascular disorders, musculoskeletal disorders, etc.), and conditions or diseases of the body as a whole. The pharmaceutical composition is particularly desirable for use in treating nervous system disorders that are indicated by symptoms of dementia. Upon administration of the pharmaceutical compositions of the present invention, it is possible to reduce the severity of dementia through enhancing cerebral cellular metabolism (i.e., improving mitochondrial function in cerebellar tissues). Thus, the pharmaceutical compositions are particularly useful as a prophylactic for delaying the onset of dementia or as a treatment for delaying the progression of dementia associated with various nervous system disorders. The pharmaceutical compositions are also useful for ameliorating the clinical manifestations of dementing illnesses by improving the function of the remaining, but often metabolically compromised, cells.

The pharmaceutical compositions of the present invention are also particularly desirable for treating diseases of the heart or other organs, where metabolic insufficiency of those organs occurs due to compromised blood supply or other causes.

Disease states that can be treated with selected compositions of the present invention include degenerative diseases of the nervous system (including but not limited to Alzheimer's Disease, Parkinson's Disease, Diffuse Lewy body disease) as well as part of the regimen for the treatment of stroke, ischemic heart disease, and other forms of vascular disease. Other selected compositions can treat depression or malignancies.

The above benefits of the present invention can be provided in a palatable formulation which provides the benefits of a sugar; a Krebs cycle intermediate, precursor of a Krebs cycle intermediate, salt thereof, or combination thereof; as well as phenylethylamine, antioxidants and/or unsaturated lipids.

BRIEF DESCRIPTION OF THE DRAWINGS

FIG. 1 illustrates the Krebs cycle and the relationship between each of its intermediates. Oxaloacetic acid and an acetyl group (from acetyl-CoA) combine to form citric acid. In the course of the cycle, two of the carbon atoms of citric acid are oxidized completely to carbon dioxide, and oxaloacetic acid is regenerated. This process generates one molecule of ATP, three molecules of NADH, and one molecule of $FADH_2$. Ultimately, the reduced cofactors NADH and $FADH_2$ are introduced into an electron transport mechanism that results in their oxidation, which yields additional molecules of ATP.

DETAILED DESCRIPTION OF THE INVENTION

The present invention relates to a pharmaceutical composition which includes a sugar in combination with a Krebs cycle intermediate or a precursor of a Krebs cycle intermediate; and a component selected from the group consisting of an unsaturated lipid (e.g., ω-3 and ω-6 fatty acids), phenylethylamine, a soluble calcium compound, a combination thereof, or a combination thereof. The composition can also contain a further ingredient to enhance mitchochondrial function (e.g., an anti-oxidant).

Krebs cycle intermediates are the acids or salts of compounds that are utilized during the Krebs tricarboxylic acid cycle. Thus, Krebs cycle intermediates include citric acid, aconitic acid, isocitric acid, α-ketoglutaric acid, succinic acid, fumaric acid, malic acid, oxaloacetic acid and mixtures thereof. Referring to FIG. 1, depending upon which Krebs cycle intermediate the pharmaceutical composition of the present invention contains, the pharmaceutical composition will be predicted ultimately to yield differing amounts of ATP. It is believed that a number of disorders involving altered oxidative metabolism include a disruption of the Krebs cycle at or prior to conversion of α-ketoglutaric acid to succinic acid. For such disorders, the pharmaceutical compositions of the present invention preferably contain a Krebs cycle intermediate such as succinic acid, fumaric acid, malic acid, oxaloacetic acid or mixtures thereof.

Precursors of Krebs cycle intermediates are compounds that, upon administration to a subject, are converted by the body (i.e., in vivo) into a Krebs cycle intermediate. Generally, mono- and di-alkyl citrates, aconitates, isocitrates, α-ketoglutarates, succinates, fumarates, malates and oxaloacetates are desirable precursors because the ester-bonds are readily broken by the body to yield the Krebs cycle intermediate. Other ester precursors may be developed using known technology for enhancing entry of the precursor molecule into affected cells. For example, U.S. Pat. No. 5,739,117 to Yokoyama, which is hereby incorporated by reference, discloses a variety of glucose ester derivatives which more effectively enter brain cells. One preferred class of precursors of Krebs cycle intermediates are compounds that are converted by the body into oxaloacetic acid or oxaloacetate. Exemplary precursors in this class include 2-keto-4-hydroxypropanol, 2,4-dihydroxybutanol, 2-keto-4-hydroxybutanol, 2,4-dihydroxybutyric acid, 2-keto-4-hydroxybutyric acid, aspartates, as well as the previously identified mono- and di-alkyl oxaloacetates. The amino acid aspartate is converted into oxaloacetic acid by the transamination reaction.

Krebs cycle intermediates or precursors of Krebs cycle intermediates which are acidic tend to be unpalatable to the patient, especially when included in a pharmaceutical formulation that is intended to be chewed or taken as an oral solution. By virtue of certain embodiments of the present invention, a calcium compound is included in order to neutralize and mask the unpleasant taste of the Krebs cycle intermediates or precursor thereof.

Suitable calcium compounds include, but are not limited to, soluble calcium salts such as calcium lactate, calcium sulfate, calcium citrate, calcium malate, calcium gluconate and combinations thereof.

The calcium compound is preferably soluble so as not to provide a chalky texture to the pharmaceutical formulation, which can be as unpleasant to the patient as an obnoxious taste.

The presence of calcium is also beneficial to the patient as it can aid in the prophylaxis of osteoporosis in the patient being administered the pharmaceutical. Further, the calcium will not have a deleterious effect on a patient with cardiovascular issues, as compared to a sodium- or potassium-containing compound.

Sugars which are suitable for use with the present invention include monosaccharides, such as glucose, fructose, mannose and galactose; disaccharides such as sucrose, maltose and lactose; and polysaccharides (i.e., starches such as amylose) that are digested by the body to form monosaccharides.

The unsaturated lipid of the present invention can be selected from, e.g., the group consisting of unsaturated monoglycerides, unsaturated diglycerides, unsaturated triglycerides, unsaturated fatty acids, unsaturated fatty alcohols, unsaturated phosphatides, unsaturated sterols, unsaturated fat-soluble vitamins, unsaturated terpenes and mixtures thereof.

Particular unsaturated lipids include high oleic acid content sunflower oil, sunflower oil, rapeseed oil, soybean oil, peanut oil, canola oil, cottonseed oil, coconut oil, palm oil, palm kernel oil, corn oil, flax seed oil, olive oil, safflower oil, fish oil and mixtures thereof.

Unsaturated fatty acids which include ω-3 and/or ω-6 fatty acids, such as fish oils and flax seed oil, are particularly preferred.

The phenylethylamine included in the pharmaceutical formulation of the present invention is preferably 2-phenylethylamine.

The pharmaceutical composition of the present invention can also include an adjuvant for enhancing mitochondrial function (i.e., oxidative metabolism). Suitable adjuvants include vitamins, minerals, antioxidants and other metabolism-enhancing compounds. B-complex vitamins are preferred for administration as adjuvants because of their involvement with metabolism. Exemplary vitamins that are useful as an adjuvant include thiamin (vitamin $B_1$), riboflavin (vitamin $B_2$), niacin (Vitamin $B_3$), pyridoxine derivatives (vitamin $B_6$) and pantothenic acid. Exemplary minerals that are useful as an adjuvant include calcium, magnesium, sodium, potassium and zinc. Exemplary antioxidants include ascorbic acid, α-tocopherol, resveratrol, quercetin and other flavonoids. Exemplary metabolism-enhancing compounds include L-carnitine and its derivatives, and creatine. Creatine supplementation is described in U.S. Pat. No. 5,767,159 to Hultman, which is hereby incorporated by reference. L-carnitine has been found to ameliorate abnormalities associated with AD in a model system (Malow et al., "Cultured Cells as a Screen for Novel Treatments of Alzheimer's Disease," Arch. Neurol. 46:1201-1203 (1989), which is hereby incorporated by reference).

Preferred antioxidants are those found in catechins and (–)-epicatechins (such as those that occur in green tea and chocolate) and curcumin (which occurs in curry spices such as turmeric).

The pharmaceutical composition of the present invention can be administered orally, by anal suppository, parenterally (for example, subcutaneously, intravenously, intramuscularly, intraperitoneally or intrathecally), by interstitial infusion, by intranasal instillation or by application to mucous membranes, such as those of the nose, throat and bronchial tubes. They may be administered alone or with suitable pharmaceutically acceptable vehicles, and can be in solid or liquid form such as tablets, capsules, powders, solutions, suspensions or emulsions.

The solid unit dosage forms can be of the conventional type, such as an ordinary gelatin capsule containing the active ingredients and a pharmaceutically acceptable vehicle. Suitable vehicles include lubricants and inert fillers. The above described sugars can also serve as fillers. In another embodiment, these compounds are tableted with conventional tablet bases (i.e., sugars as described above) in combination with binders like acacia, gum tragacanth, cornstarch or gelatin; disintegrating agents such as cornstarch, potato starch or alginic acid; a lubricant such as stearic acid or magnesium stearate; and sweetening agents such as the above described sugars, saccharine or aspartame; and flavoring agents such as peppermint oil, oil of wintergreen or artificial flavorings.

The pharmaceutical compositions of the present invention may also be administered in injectable dosages by solution or suspension of these materials in a physiologically acceptable diluent with a pharmaceutical vehicle. Such vehicles include sterile liquids such as water and oils, with or without the addition of a surfactant and other pharmaceutically acceptable adjuvants such as those described above. Illustrative oils are those of petroleum, animal, vegetable or synthetic origin, for example, peanut oil, soybean oil or mineral oil. In general, water, saline, aqueous sugar solutions formed with the above-described sugars, and glycols such as polypropylene glycol or polyethylene glycol, are preferred liquid vehicles, particularly for injectable solutions. In order to maintain sterility and prevent action of microorganisms, antibacterial and antifungal agents, such as parabens, chlorobutanol, phenol, ascorbic acid, thimerosal and the like, may be added to the vehicle.

In certain embodiments, the pharmaceutical formulations are in the form of edible or drinkable compositions, e.g., foodstuffs such as chewable or edible bars, confectionary products (e.g., chocolate bars), cookies, juice drinks, baked or simulated baked goods (e.g., brownies), biscuits, lozenges or chewing gum. Preferred chewable or edible bars include chocolate bars and brownies. Such embodiments are beneficial as they provide the benefits as disclosed above and also provide the benefit of relieving hunger or fatigue. Such formulations can be particularly useful to people participating in sports or other forms of exercise.

In certain embodiments, a sugar (e.g., glucose) can be utilized to improve flavor and satisfaction. A preferred embodiment includes calcium malate, resveritrol, and flax seed oil to fortify the healthy effects of the edible or drinkable product.

In certain embodiments (e.g., chocolate products), various flavors can be included in the product such as orange, lemon, cherry, bourbon, Irish whiskey, brandy and the like.

In certain embodiments, the invention is directed to a chocolate food product comprising cocoa, edible filler and added 2-phenylethylamine, wherein the ratio of the amount of 2-phenylethylamine in the product as compared to the 2-phenylethylamine provided by the cocoa and edible filler is at least 2:1; at least 10:1; at least 50:1; at least 100:1; at least 500:1; or at least 1000:1.

In certain embodiments, the foodstuff can be in the form of icing on a food product (e.g., cookie) or a spread between two food products (e.g., cookies), wherein the beneficial ingredients of the present invention can be in the icing/spread, the other food product, or both. Such an embodiment is useful for those who do not tolerate chocolate.

The pharmaceutical composition of the present invention is useful for augmenting cellular metabolism in subjects (e.g., patients) who suffer from a disorder characterized by abnormally decreased levels of oxidative metabolism. It is believed that administration of the pharmaceutical composition of the present invention enhances the ability of cells to regulate themselves in a healthy state, i.e., to maintain homeostasis. It does this, in part, by enhancing mitochondrial function by augmenting operation of the Krebs cycle. Administering sugar to a subject provides a carbon source for producing acetyl groups and administering the Krebs cycle intermediate or the precursor of a Krebs cycle intermediate to a subject increases the concentration of the particular Krebs cycle intermediate at the mitochondrial level. It is believed that this has a priming effect, because a four carbon intermediate is needed in order for the two-carbon derivatives of glucose and other substrates to enter the Krebs cycle. Specifically, the two-carbon acetyl group must combine with the four-carbon oxaloacetate to form citrate in order for the Krebs cycle to continue. Malate is in equilibrium with oxaloacetate, and other Krebs cycle intermediates are readily converted to malate and oxaloacetate. The conversion of succinate and fumarate to malate and oxaloacetate is particularly rapid. Metabolically compromised cells tend to utilize Krebs cycle intermediates for the direct generation of energy. More specifically, they utilize the intermediates to generate electrons that then generate ATP through electron transport. While utilizing the intermediates provides an immediate source of energy, doing so compromises the subsequent activity of the Krebs cycle. Administration of the pharmaceutical compositions of the present invention is believed, therefore, to prime the Krebs cycle so that it again operates efficiently.

Thus, another aspect of the present invention relates to a method of treating a subject having a disorder involving impaired mitochondrial function. Generally, the method includes administering the pharmaceutical composition of the present invention to a subject under conditions effective to improve mitochondrial function.

This method of the present invention is particularly useful for the treatment or prophylaxis of disorders associated with impaired mitochondrial function. Disorders that can be treated according to this method generally include conditions or diseases characterized by a decreased level of oxidative metabolism. The disorders may be caused by genetic factors, environmental factors or both. More specifically, such disorders include conditions or diseases of the nervous system (e.g., neurodegenerative, psychoses, etc.), conditions or diseases of other parts of the body, and conditions or diseases of the body as a whole. Exemplary conditions or diseases of the nervous system include Alzheimer's Disease, Parkinson's Disease, Huntington's Disease, spinocerebellar ataxias, and psychoses (including depression or schizophrenia) associated with oxidative metabolic abnormalities. Exemplary conditions or disorders of other parts of the body include cardiovascular disorders (e.g., atherosclerotic and cardiovascular diseases including myocardial infarctions, angina, cardiomyopathies, cardiac valvular disorders, and other conditions or disorders causing cardiac failure), musculoskeletal disorders in which oxidative metabolism is abnormal (De Coo et al., A Mitochondrial tRNA(Val) Gene Mutation (G1642A) in a Patient With Mitochondrial Myopathy, Lactic Acidosis, and Stroke-like Episodes," Neurol. 50:293-295 (1998), which is hereby incorporated by reference), and other conditions or disorders of non-neural tissues in which oxidative metabolism is abnormal, such as frailty, which is a recognized geriatric syndrome often associated with metabolic alterations (Fayette et al., Eur. J. Clin. Nutrition 52:45-53 (1998), which is hereby incorporated by reference).

Many conditions or diseases of the nervous system (e.g., Alzheimer's Disease and those described above) are characterized by cerebral metabolic insufficiencies, which are manifested as impaired cerebral function such as dementia. Therefore, another aspect of the present invention relates to a method of improving cerebral function in a subject having cerebral metabolic insufficiencies. Generally, a pharmaceutical composition of the present invention is administered to a subject having impaired cerebral metabolism under conditions effective to improve the cerebral cellular metabolism. By improving cerebral cellular metabolism, the subject's cerebral function is improved significantly.

Treatment for nervous system disorders typically involves administration of the pharmaceutical composition of the present invention so that the Krebs cycle intermediate or the precursor of a Krebs cycle intermediate is introduced into brain tissue. To exert its desired therapeutic or prophylactic effects, the sugar and the Krebs cycle intermediate or the precursor of a Krebs cycle intermediate must be transported into the brain cells, and subsequently the Krebs cycle intermediate and derivatives of the sugar (e.g., pyruvate, acetate)

must be incorporated into the brain cell mitochondria (i.e., where they may be incorporated into the Krebs cycle).

Depending upon how the pharmaceutical composition of the present invention is administered (e.g., oral preparation, intravenous injection, etc.) and the conditions of the patient to be treated, effective administration may require overcoming the cerebrovascular endothelium, also called the blood-brain barrier ("BBB"). The BBB is formed by cerebral endothelial cells under the influence of astroglial cells of the brain (Johansson, "Experimental Models of Altering the Blood Brain Barrier," Progress in Brain Research, 91:171-175 (1992); Ermisch, "Peptide Receptors of the Blood-Brain Barrier and Substrate Transport into the Brain," Progress in Brain Research, 91:155-161 (1992), which are hereby incorporated by reference). The BBB contains a monolayer of tightly connected microvascular endothelial cells with anionic charges, which layer separates two fluid-containing compartments: the blood plasma and extracellular fluid of the brain parenchyma. One of the main functions of the BBB is to regulate the transfer of components between blood plasma and extracellular fluid. The BBB limits free passage of molecules from the blood to the brain cells. This limited penetration into the CNS is noticeable with large molecules of high polarity such as protein conjugates, enzymes, etc. (Bobo et al., "Convection-enhanced Delivery of Macromolecules in the Brain," Proc. Natl. Acad. Sci. USA, 91:2076-2080 (1994), which is hereby incorporated by reference).

According to one approach, the BBB is circumvented according to any of a variety of known strategies, for example, intrathecal injections (Ommaya, "Implantable Devices for Chronic Access and Drug Delivery to the Central Nervous System," Cancer Drug Delivery, 1(2): 169-179 (1984), which is hereby incorporated by reference), surgical implants (U.S. Pat. No. 5,222,982 to Ommaya, which is hereby incorporated by reference), and interstitial infusion (Bobo et al., "Convection-enhanced Delivery of Macromolecules in the Brain," Proc. Natl. Acad. Sci. USA, 91:2076-2080 (1994), which is hereby incorporated by reference). Each of these strategies involves delivery of the Krebs cycle intermediate or the precursor of a Krebs cycle intermediate to the central nervous system by direct administration into the cerebrospinal fluid or into the brain parenchyma.

According to another approach, the Krebs cycle intermediate or the precursor of a Krebs cycle intermediate is linked to a molecule that enhances crossing of the BBB. Various BBB crossing enhancers have been identified (e.g., permeabilizer peptides), and others are continually being identified.

As described above, the pharmaceutical composition of the present invention is useful for treating a subject having a nervous system disorder that involves impaired mitochondrial function. Several nervous system disorders are known to involve deficiencies in neurotransmitter systems. For example, Alzheimer's Disease is associated with degeneration of cholinergic neurons in the basal forebrain that play a fundamental role in cognitive functions, including memory (Becker et al., "Mechanisms of Cholinesterase Inhibition in Senile Dementia of the Alzheimer Type: Clinical, Pharmacological, and Therapeutic Aspects," Drug Dev. Res. 12: 163-195 (1988)). As a result of such degeneration, patients suffering from the disease exhibit a marked reduction in acetylcholine synthesis, choline acetyltransferase activity, acetylcholinesterase activity and choline uptake. There have been several approaches employed to treat Alzheimer's Disease. These generally include the administration of acetylcholinesterase inhibitors or acetylcholine synthesis, storage or release modulators. Also, since activation of NMDA glutamate receptors has also been implicated in the etiologies of Huntington's Disease, amyotrophic lateral sclerosis, olivopontocerebellar atrophy and Alzheimer's Disease, use of NMDA glutamate receptor antagonists may be of clinical benefit for patients having these disorders (Woodruff et al., "The Interaction Between MK-801 and Receptors for N-methyl-D-aspartate: Functional Consequences," Neuropharm. 26:903-909 (1987); Greenamyre et al., "N-methyl-D-aspartate Antagonists in the Treatment of Parkinson's Disease," Arch. Neurol. 48:977-981 (1991); Giuffra et al., "Glutamatergic Therapy of Huntington's Chorea," Clin. Neuropharm. 15:148-151 (1992), which are hereby incorporated by reference), as well as for patients suffering from certain neurodegenerative effects of aging (Ferris, S. H. "Therapeutic Strategies in Dementia Disorders" Acta Neurol. Scand. 129 (Suppl.):23-26 (1990), which is hereby incorporated by reference). With respect to agents used in the treatment of PD, L-dopa and its derivatives are primary therapeutic agents.

For treatment of certain nervous system disorders, therefore, the pharmaceutical composition of the present invention can be administered either alone or in combination with a therapeutic agent for the treatment of a nervous system disorder. Suitable therapeutic agents include conventional medications for treating such nervous system disorders. By way of example, for treatment of Alzheimer's Disease, the pharmaceutical composition can be administered in combination with either an acetylcholinesterase inhibitor, an acetylcholine synthesis, storage or release modulator, an NDMA glutamate receptor antagonist, or combinations thereof. A number of suitable acetylcholinesterase inhibitors, acetylcholine synthesis, storage or release modulators, and NDMA glutamate receptor antagonists are currently known and others are continually being discovered and reported.

As described above, the pharmaceutical composition of the present invention is useful for treating a subject having a cardiovascular disorder that involves impaired mitochondrial function. For treatment of certain cardiovascular disorders, therefore, the pharmaceutical composition of the present invention can be administered either alone or in combination with conventional agents for the treatment of cardiovascular disorders. By way of example, the pharmaceutical composition of the present invention can be administered simultaneously with either blood-thinners, cholesterol lowering agents, anti-platelet agents, vasodilators, beta-blockers, angiotensin blockers, digitalis and its derivatives, and combinations thereof. A number of suitable blood-thinners, cholesterol lowering agents, anti-platelet agents, vasodilators, beta-blockers, angiotensin blockers and digitalis derivatives are currently known and others are continually being discovered and reported.

As described above, the pharmaceutical composition of the present invention is useful for treating a subject having a musculoskeletal disorder that involves impaired mitochondrial function. For treatment of certain musculoskeletal disorders, therefore, the pharmaceutical composition of the present invention can be administered either alone or in combination with conventional agents for the treatment of musculoskeletal disorders.

EXAMPLES

The following Examples are provided to illustrate embodiments of the present invention but are by no means intended to limit its scope.

Example 1

Fudge

Components:
unsweetened chocolate (30 gms)
flax seed oil (20 gm, i.e. 2 tablespoons)
glucose (50 gm)

calcium malate (13.4 gm)
green tea powder, from uncooked green tea leaves (4.7 gm; 1 teaspoon)
resveratrol (20 mg)
Formulation:

Melt chocolate and mix with flax seed oil. Stir in glucose, then calcium malate, then reserveratrol, then green tea powder. The mixture should be soft when formed. Then chill in the refrigerator (4° C.) until firm. This preparation retains the firm consistency of a normal bar of chocolate at room temperature, but it is routinely stored at refrigerator temperature.

The fudge of Example 1 can be used as an adjunct (i.e., part of the regimen) for treatment of degenerative diseases of the nervous system (including but not limited to Alzheimer's Disease, Parkinson's Disease, Diffuse Lewy body disease) as well as part of the regimen for the treatment of stroke, ischemic heart disease, and other forms of vascular disease. The fudge of Example 1 can also be used to help prevent the development of these diseases in individuals at risk for them.

Example 2

Fudge

This preparation is identical to Example 1, except that 3 mg of phenylethylamine is added to the flax oil before it is mixed into the unsweetened chocolate.

The fudge of Example 2 can be used in the same uses as Example 1, but in individuals who are apathetic or depressed and do not develop headaches, excitement or other significant side effects to the ingestion of phenylethylamine.

Example 3

Fudge

The fudge of Example 3 is identical to the fudge of Example 1, except that it also contains curcumin. The curcumin (100 μg) is added immediately before the resveratrol. Alternatively, the fudge of Example 3 can be prepared in accordance with Example 2, except for also containing curcumin (100 μg) which can be added immediately before the reserveratrol.

The fudge of Example 3 can be used as an adjuvant to treatment of individuals with malignancies (i.e., cancers), or in the attempted prevention of the development of recurrent or other cancers.

Example 4

Juice Drink

Components:
unsweetened, organic (e.g., Knudsen brand) grape juice (16 fluid ounces)
phenylethylamine (1 microliter=1 μl)
resveratrol (20 mg)
glucose (50 gm)
calcium malate (1.4 gm)
green tea powder, from uncooked green tea leaves (4.7 gm; 1 teaspoon)
Formulation:
The other components are added to the grape juice in the order that are listed. The drink is kept at refrigerator temperature.

The drink of Example 4 can be used as an energizing health drink in adults or elderly, and further includes uses by the military.

Example 5

Juice Drink

Components:
unsweetened, organic (e.g., Knudsen brand) grape juice (16 fluid ounces)
phenylethyl-2-amine (6 mg)
resveratrol (20 mg)
glucose (80 gm)
calcium malate (0.2 gm)
Formulation:
The other components are added to the grape juice in the order that are listed. The drink is kept at refrigerator temperature. Suggested amount: 4 ounces at a time.

Example 6

Chocolate

Components:
Chocolate, baker, high grade, dark, unsweetened (10 gm)
2-Phenylethylamine (3 mg) and
resveratrol (15 mg), both dissolved in 7.5 ml of organic flax seen oil
glucose (20 gm)
calcium malate (120 gm)
Suggested amount: 1 preparation after a light salad lunch.

It is understood that one skilled in the art can make obvious variations to the embodiments disclosed herein. These obvious variations are meant to be encompassed by the appended claims.

The invention claimed is:

1. A method of treating a disease associated with impaired mitochondrial function chosen from the group consisting of a nervous system disorder, a cardiovascular disorder and a musculoskeletal disorder,
   the nervous system disorder being chosen from the group consisting of Alzheimer's Disease, Huntington's Disease, Parkinson's Disease, spinocerebellar ataxia and a psychosis,
   the cardiovascular disorder being selected from the group consisting of atherosclerotic cardiovascular disease, cardiomyopathies and cardiac valvular disorders, and
   the musculoskeletal disorder consisting of mitochondrial myopathy,
   said method comprising administering to a patient in need thereof a pharmaceutical composition comprising:
   a sugar;
   a Krebs cycle intermediate, precursor of a Krebs cycle intermediate, salt thereof, or combination thereof; and
   a component selected from the group consisting of an unsaturated lipid, a soluble calcium compound, or a combination thereof.

2. The method according to claim 1, wherein said administering is oral, rectal, parenteral, or by application to mucous membranes.

3. The method of claim 1, wherein the pharmaceutical composition is in the form of an edible solid or liquid.

4. The method of claim 3, wherein the edible solid is in the form of a confectionary product.

5. The method of claim 3, wherein the edible liquid comprises a fruit juice.

6. The method of claim 1, wherein the pharmaceutical formulation is in the form of chewable or edible bars, confectionary products, cookies, baked or simulated baked goods, biscuits, lozenges, juice drinks or chewing gum.

7. The method of claim 1, wherein the pharmaceutical composition is in the form of an oral solid dosage form, a parenteral product, an intramucosal product or a suppository.

8. The method of claim 1, wherein the unsaturated lipid in the pharmaceutical composition is selected from the group consisting of unsaturated monoglycerides, unsaturated diglycerides, unsaturated triglycerides, unsaturated fatty acids, unsaturated fatty alcohols, unsaturated phosphatides, unsaturated sterols, unsaturated fat-soluble vitamins, unsaturated terpenes, and mixtures thereof.

9. The method of claim 1, wherein the unsaturated lipid in the pharmaceutical composition is selected from the group consisting soybean oil, peanut oil, and mixtures thereof.

10. The of claim 1, wherein the soluble calcium compound in the pharmaceutical composition is selected from the group consisting of calcium lactate, calcium sulfate, calcium citrate, calcium malate, calcium gluconate and combinations thereof.

11. The method of claim 10, wherein the soluble calcium compound in the pharmaceutical composition is calcium malate.

12. The method of claim 1, wherein the Krebs cycle intermediate in the pharmaceutical composition is selected from a group consisting of citric acid, aconitic acid, isocitric acid, a-ketoglutaric, succinic acid, fumaric acid, malic acid, oxaloacetic acid, and combinations thereof.

13. The of claim 1, wherein the precursor in the pharmaceutical composition is selected from a group consisting of 2,4-dihydroxybutanol, 2-keto-4-hydroxybutanol, 2,4-dihydroxybutyric acid, 2-keto-4-hydroxybutyric acid, aspartate, mono-alkyl esters of oxaloacetate, di-alkyl esters of oxaloacetate, and mixtures thereof.

14. The method of claim 1, wherein the sugar in the pharmaceutical composition is selected from the group consisting of a monosaccharide, disaccharide, polysaccharide, and mixtures thereof.

15. The method of claim 13, wherein the monosaccharide is selected from a group consisting of glucose, fructose, mannose, galactose, and mixtures thereof.

16. The method of claim 13, wherein the disaccharide is selected from a group consisting of sucrose, maltose, lactose, and mixtures thereof.

17. The method of claim 13, wherein the polysaccharide is a starch.

18. The method of claim 1, wherein the pharmaceutical composition further comprises a mitochondrial function enhancing compound.

19. The method of claim 18, wherein the mitochondrial function enhancing compound is selected from the group consisting of a vitamin, a mineral, an antioxidant, a metabolism-enhancing compound, and mixtures thereof.

20. The method of claim 19, wherein the metabolism-enhancing compound is selected from the group consisting of creatine, L-carnitine, L-carnitine derivatives, and mixtures thereof.

21. The method of claim 19, wherein the vitamin is selected from the group consisting of thiamin, riboflavin, niacin, pyridoxine derivatives, pantothenic acid, and mixtures thereof.

22. The method of claim 19, wherein the mineral is selected from the group consisting of calcium, magnesium, sodium, potassium, zinc, and mixtures thereof.

23. The method of claim 19, wherein the antioxidant is selected from the group consisting of ascorbic acid, alpha-tocopherol, resveritrol, quercetin, and mixtures thereof.

24. The method of claim 1, wherein the pharmaceutical composition further comprises at least one pharmaceutically acceptable excipient.

* * * * *